(12) United States Patent
Ward et al.

(10) Patent No.: US 9,499,666 B2
(45) Date of Patent: Nov. 22, 2016

(54) BENZOXAZINES AND COMPOSITIONS CONTAINING THE SAME

(71) Applicant: Cytec Technology Corp., Wilmington, DE (US)

(72) Inventors: Steven Ward, Chester (GB); Mark Harriman, Northallerton (GB)

(73) Assignee: Cytec Technology Corp., Wilmington, DE (US)

( * ) Notice: Subject to any disclaimer, the term of this patent is extended or adjusted under 35 U.S.C. 154(b) by 75 days.

(21) Appl. No.: 13/848,220

(22) Filed: Mar. 21, 2013

(65) Prior Publication Data

US 2013/0267659 A1    Oct. 10, 2013

(30) Foreign Application Priority Data

Mar. 29, 2012 (GB) .................... 1205574.5

(51) Int. Cl.
```
C08G 73/02      (2006.01)
C08L 79/02      (2006.01)
C07D 265/16     (2006.01)
C08J 5/24       (2006.01)
C08K 5/357      (2006.01)
C08G 59/00      (2006.01)
C08G 14/06      (2006.01)
C08L 61/34      (2006.01)
```

(52) U.S. Cl.
CPC ......... *C08G 73/0233* (2013.01); *C07D 265/16* (2013.01); *C08G 14/06* (2013.01); *C08G 59/00* (2013.01); *C08J 5/24* (2013.01); *C08K 5/357* (2013.01); *C08L 61/34* (2013.01); *C08L 79/02* (2013.01)

(58) Field of Classification Search
USPC ................. 525/495, 500; 428/320.2
See application file for complete search history.

(56) References Cited

U.S. PATENT DOCUMENTS

| | | | |
|---|---|---|---|
| 5,543,516 A | 8/1996 | Ishida | |
| 6,225,440 B1 | 5/2001 | Ishida | |
| 7,537,827 B1 * | 5/2009 | Lehmann et al. | 428/297.1 |
| 7,649,037 B1 * | 1/2010 | Li et al. | 524/87 |
| 7,947,802 B2 | 5/2011 | Ishida et al. | |
| 8,119,307 B2 * | 2/2012 | Choi et al. | 429/524 |
| 8,536,283 B2 * | 9/2013 | Tzou et al. | 525/504 |
| 2007/0275285 A1 | 11/2007 | Choi et al. | |
| 2008/0045688 A1 | 2/2008 | Lin et al. | |
| 2008/0145743 A1 * | 6/2008 | Choi et al. | 429/43 |
| 2009/0270615 A1 | 10/2009 | Taden et al. | |
| 2010/0140542 A1 | 6/2010 | Ji et al. | |
| 2010/0204400 A1 | 8/2010 | Kreiling et al. | |
| 2010/0330287 A1 | 12/2010 | Tietze et al. | |
| 2011/0172356 A1 | 7/2011 | Kreiling et al. | |
| 2011/0274907 A1 * | 11/2011 | Steele et al. | 428/297.4 |
| 2012/0077402 A1 * | 3/2012 | Grasser et al. | 442/179 |

FOREIGN PATENT DOCUMENTS

| | | | |
|---|---|---|---|
| WO | 00/00535 A1 | 1/2000 | |
| WO | 00/61650 A1 | 10/2000 | |
| WO | 2007/064801 A1 | 6/2007 | |
| WO | 2012/015604 A1 | 2/2012 | |

OTHER PUBLICATIONS

R. Andreu et al: "Studies on the thermal polymerization of substituted benzoxazine monomers: Electronic effects", Journal of Polymer Science Part A: Polymer Chemistry; vol. 46, No. 10; Apr. 14, 2008.

Shengfang Li et al: "Synthesis, characterization, and polymerization of brominated benzoxazine monomers and thermal stability/flame retardance of the polymers generated", Polymers for Advanced Technologies, vol. 21, No. 4; Mar. 17, 2009.

International Search Report. PCT/US2013/032897. Jun. 4, 2013.

* cited by examiner

*Primary Examiner* — Tae H Yoon

(74) *Attorney, Agent, or Firm* — Thi D. Dang

(57) ABSTRACT

Disclosed herein are monofunctional benzoxazine compounds having at least one electron-withdrawing group. The monofunctional benzoxazine compounds may be combined with one or more multifunctional benzoxazine compounds to form a unique benzoxazine blend. This benzoxazine blend may be combined with additional components such as catalysts and toughening agents to form a curable resin composition suitable for forming resinous films or composite materials. The presence of monofunctional benzoxazine improves the processability of the benzoxazine-based resin composition by reducing the viscosity of the resin composition, and results in improved tack and drape in the films and composite materials formed from the composition without the loss of modulus in the cured resin.

15 Claims, 10 Drawing Sheets

Fluorinated Liquid Benzoxazine Blends

95:5　　　　　90:10　　　　　80:20　　　　　50:50
Alkylated liquid benzoxazine blends

BENZOXAZINES AND COMPOSITIONS CONTAINING THE SAME

BACKGROUND

The use of benzoxazines offers a number of advantages as compared to other thermosetting resins including relatively long shelf-life, molecular design flexibility, low cost, high glass transition temperature ($T_g$), high modulus, relatively low viscosities, good flame retardant properties, low moisture absorption, no by-products released during curing and very low shrinkage upon curing. Furthermore, benzoxazines are capable of being self-cured upon heating; i.e. there is no need for an additional curing agent. This combination of properties means benzoxazines are potentially attractive for use in aerospace applications. In particular they may be useful as the thermosetting matrix in composite materials. However, currently available multifunctional benzoxazines are glassy solids at temperatures below 120° C. making them difficult to process using standard aerospace techniques such as prepregging and resin infusion.

"Prepregging" refers to the process of impregnating unidirectionally aligned reinforcing fibers or woven fabric with a resin matrix to form prepregs in the form of tapes or sheets. These prepregs are then layered onto each other in a particular orientation on a tool to form a laminate. The prepreg lay-up is then subjected to elevated temperature and pressure to cure and consolidate the composite part. The method of pressure application is dependent on the part and configuration, but the use of an autoclave is most common for high-performance structural parts. The prepregs must have a certain amount of tack and drape in order to mold properly. "Tack" is the ability of prepreg plies to stick together, while "drape" is the ability of the prepreg to conform to different contours.

Resin infusion approach differs from that of conventional prepregging in that dry structural reinforcement fibers are placed into a mold cavity or other shaping tool, and a matrix resin is injected or infused into the structural reinforcement fibers. Resin infusion covers processing techniques such as Resin Transfer Molding (RTM), Liquid Resin Infusion (LRI), Resin Infusion under Flexible Tooling (RIFT), Vacuum Assisted Resin Transfer Molding (VARTM), Resin Film Infusion (RFI) and the like. Such conventional techniques require the resins to be of relatively low viscosity and to be thermally stable at processing temperatures.

SUMMARY

Disclosed herein is a benzoxazine blend containing one or more monofunctional benzoxazine compounds having at least one electron-withdrawing group and one or more multifunctional benzoxazine compounds. This benzoxazine blend is combinable with additional components such as catalysts and toughening agents to form a curable resin composition suitable for forming resinous films or composite materials. The presence of monofunctional benzoxazine improves the processability of the benzoxazine-based resin composition by reducing the viscosity of the resin composition, and results in improved tack and drape in the films and composite materials formed from the composition without the loss of modulus in the cured resin. Through the addition of the electron withdrawing group, the monofunctional benzoxazine compounds offer increased stability at the high temperatures that are typically used in the curing cycles of aerospace applications as compared to the currently available benzoxazine systems. A further benefit of the electron withdrawing group is a decrease in the cure onset temperature, thereby allowing for beneficial modifications to the curing cycles.

DETAILED DESCRIPTION

Figure 1:
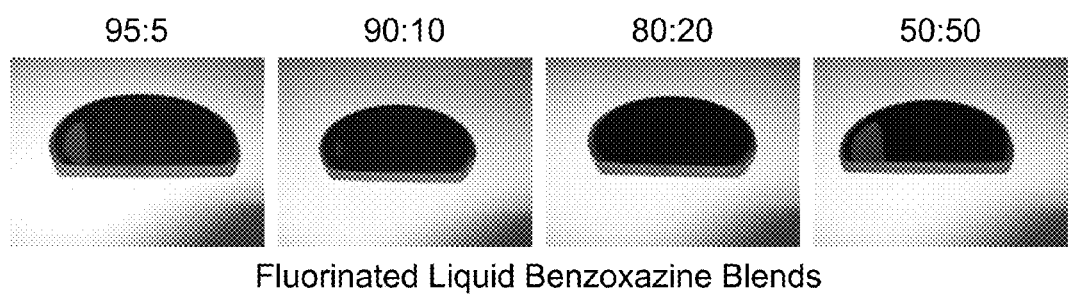
FIG. 1 shows cured samples based on different blends of Bisphenol A-benzoxazine and fluorinated liquid benzoxazine formed from 3-fluorophenol and m-toluidine.

One aspect of the present disclosure is to provide a benzoxazine blend that retains all of the beneficial properties of neat multifunctional benzoxazines, and at the same time, exhibits thermal mechanical properties suitable for high-performance aerospace applications. Currently available multifunctional benzoxazines are latent until heat is applied and typically require cure temperatures of 180° C. or greater. Several benzoxazine hybrid systems based on epoxy-benzoxazine blends are commercially available, but the addition of the epoxy as a co-reactant negates some of the benefits brought on by neat benzoxazines. Liquid monofunctional benzoxazines are also available but they suffer from being very unstable at temperatures normally used for curing cycles in aerospace applications. It has been discovered that certain substituted monofunctional benzoxazines may be mixed with multifunctional benzoxazines to improve the processability of the multifunctional benzoxazine system, which are normally solid or semi-solid at room temperature. The benzoxazine blend is combinable with additional components such as toughening agents and catalysts to form a curable resin composition, which is suitable for forming resinous films (e.g. surfacing films, adhesive films) or advanced composite materials (e.g. prepregs) using conventional techniques such as prepregging and resin infusion. The presence of liquid monofunctional benzoxazine improves the processability of the benzoxazine-based resin composition by reducing the viscosity of the uncured composition, making it suitable for impregnation/infusion of reinforcing fibers. Furthermore, the presence of liquid monofunctional benzoxazine improves the handling characteristics (e.g. tack and drape) of the uncured (or partially cured) composite material (e.g. prepreg) made from the benzoxazine-based resin composition without a loss of modulus in the cured resin. Two physical properties desired of film adhesives and prepregs are tack and drape at their intended use temperature. Tack is necessary to ensure correct placement of the prepreg when laying up composite parts. Drape is necessary in order that the composite parts having shapes other than planar may be easily fabricated. As such, benzoxazine-based resins with increased tack and drape enable the fabrication of composite parts with complex shapes.

As used herein, "monofunctional benzoxazine" refers to a compound in which there is a single benzoxazine moiety, and "multifunctional benzoxazine" refers to a compound in which there are two or more benzoxazine moieties, thereby enabling the formation of cross-linked network.

The substituted monofunctional benzoxazines of the present disclosure are based on electron-withdrawing substituted derivatives, and could be in liquid form at ambient temperature (20° C.-25° C.). Through the addition of the electron-withdrawing groups, these substituted monofunctional benzoxazines offer increased stability at the high temperatures typically used in aerospace cure cycles (e.g. 180° C. or greater) compared to the currently available liquid benzoxazines. A further benefit of the electron-withdrawing group is a decrease in the cure onset temperature allowing for beneficial modifications to the cure cycle. As such, these monofunctional benzoxazines are particularly suitable for use in aerospace applications due to the increase in thermal stability over currently available liquid benzoxazines, thereby allowing for the blending of monofunctional benzoxazines with multifunctional benzoxazines, and subsequent curing at high temperature without degradation. Furthermore, the presence of monofunctional benzoxazines with the electron-withdrawing groups in benzoxazine systems containing multifunctional benzoxazines has been found to lower the activation energy which decreases the temperature at which they react. Without being bound to any particular theory, it is believed that the decreased cure onset is a consequence of the intermediate or transition state of the monofunctional benzoxazine structure being more stable, thus, less energy is needed to initiate polymerization. Additionally, a decrease in cure onset temperature could allow for the use of lower temperature cure cycles, the removal of the post cure time, or curing with a shorter cure time as compared to benzoxazine systems with no electron-withdrawing substituents. These benefits are observed without a loss of glass transition temperature ($T_g$) or modulus in the cured resin. The "modulus" of the cured resin, as discussed herein, includes flexural modulus and tensile modulus.

The substituted monofunctional benzoxazine discussed above is a compound represented by the following Formula I:

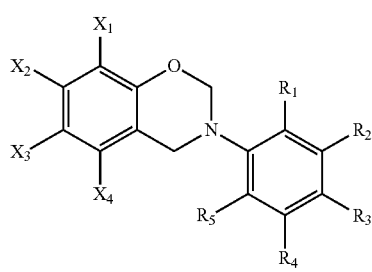

(I)

wherein:
at least one of $X_1$, $X_2$, $X_3$, $X_4$ is an electron-withdrawing group selected from a halogen (such as F, Cl, Br, I), —COH, —COCH$_3$, —COOCH$_3$, —SO$_3$H, NO$_2$, CF$_3$, or CCl$_3$, and the others are independently selected from hydrogen (H), alkyl (preferably $C_{1-8}$ alkyl), cycloalkyl (preferably $C_{5-7}$ cycloalkyl, more preferably $C_6$ cycloalkyl), and aryl, wherein the cycloalkyl and aryl groups are optionally substituted, for instance by $C_{1-8}$ alkyl, halogen and amine groups, and preferably by $C_{1-8}$ alkyl;

$R_1$, $R_2$, $R_3$, $R_4$, $R_5$ are independently selected from: H; alkyl (preferably $C_{1-8}$ alkyl); cycloalkyl (preferably $C_{5-7}$ cycloalkyl, more preferably $C_6$ cycloalkyl); aryl; wherein the cycloalkyl and aryl groups are optionally substituted, for instance by $C_{1-8}$ alkyl, halogen and amine groups, and preferably by $C_{1-8}$ alkyl; an electron-donating group such as alkoxy (e.g. methoxy —OCH$_3$), —CH3, phenyl, —NH-COR, OCOR, NH$_2$, and OH.

Examples of substituted monofunctional benzoxazine include the following structures:

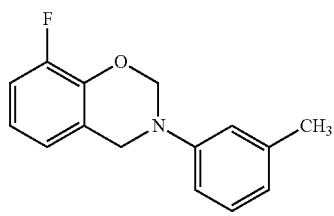

(1)

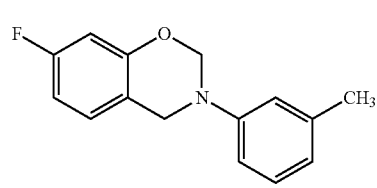

(2)

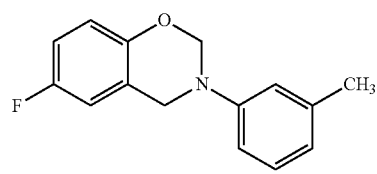

(3)

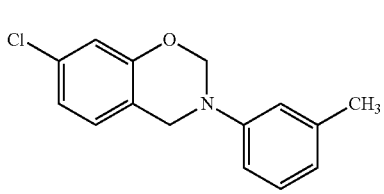

(4)

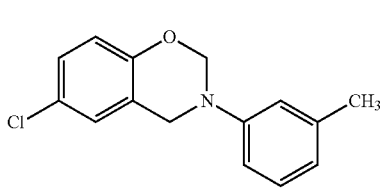

(5)

It has been found that the effect of the halogen group in the meta position (Structures 2 and 4) is the greatest on reactivity, as such this position is most preferred.

The substituted monofunctional benzoxazine compound discussed above is a reaction product of a phenol (represented by Formula II), an aromatic amine (represented by Formula III), and an aldehyde.

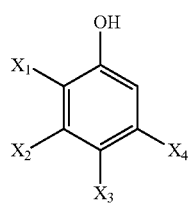

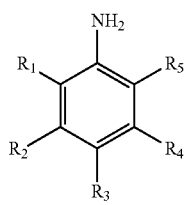

$X_1$, $X_2$, $X_3$, $X_4$ in Formula II and $R_1$, $R_2$, $R_3$, $R_4$, $R_5$ in Formula III are as defined above in reference to Formula I. Although various aldehydes may be used, the preferred aldehyde is formaldehyde (H—CHO).

The substituted monofunctional benzoxazine compounds may be formed by ring formation in a compatible solvent or in a solventless system. The synthesis of monofunctional benzoxazine monomers using phenol, amine and aldehyde as reactants is well known in the art. Generally, the reactants are mixed at a temperature which causes the reactants to combine chemically, and the reactants are maintained at this temperature for a time period sufficient to form the benzoxazine compounds.

In some embodiments, the monofunctional benzoxazine compounds with halogen substituents may be formed by reacting halogenated phenol with aromatic amine in the presence of formaldehyde or paraformaldehyde as represented by the following exemplary reaction:

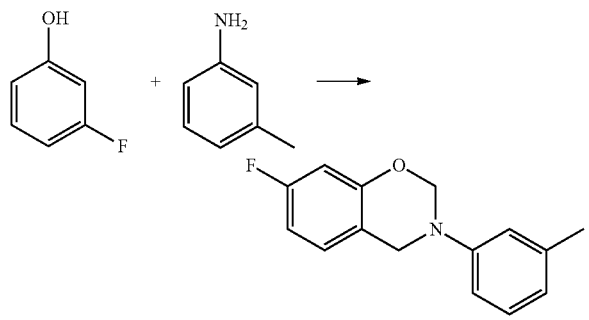

For the above type of reaction, it should be noted that, when the electron-withdrawing substituent on the phenol compound is in the meta position as shown, the benzoxazine product formed will be a blend of isomers represented by the following structures:

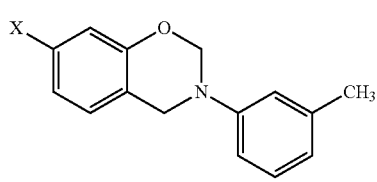

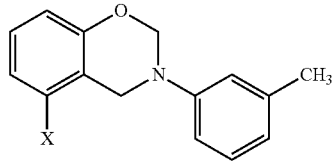

wherein X is a halogen such as fluorine (F) or chlorine (Cl).

When synthesized, this isomer blend may exist as a blend with the ratio of compound (IV) to compound (V) in the range of 70:30 to 80:20.

In one embodiment, the substituted monofunctional benzoxazine contains both an electron-withdrawing substituent and an electron-donating substituent. It has been discovered that the presence of the electron-donating substituent further enhances reactivity during polymerization. As an example, a halogenated phenol may be reacted with an amine having —OCH$_3$ as an electron-donating substituent and formaldehyde to form a substituted monofunctional benzoxazine as follows:

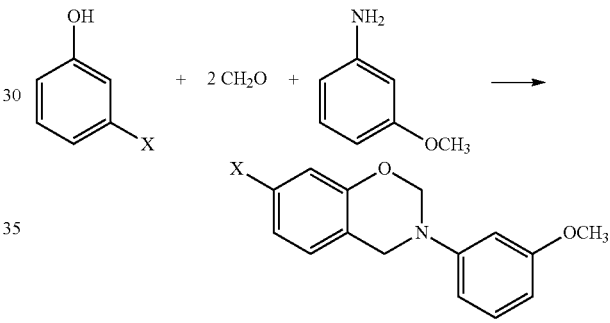

wherein X is a halogen such as fluorine (F) or chlorine (Cl).

As discussed previously, one or more of the substituted monofunctional benzoxazine compounds discussed above may be mixed with one or more multifunctional benzoxazine compounds to form a benzoxazine blend that is combinable with additional components such as tougheners and catalysts to form a curable resin composition. The total amount of monofunctional and multifunctional benzoxazines in the resin composition may be adjusted to obtain the desired properties for the uncured composition (such as reactivity, viscosity, tack and drape) and in the cured composition (such as $T_g$, modulus, toughness etc). The viscosity of the curable resin composition may be adjusted by the appropriate proportions of monofunctional and multifunctional benzoxazines to achieve certain $T_g$ for the uncured resin and to impart the required tack and drape to the uncured composite material (e.g. prepreg) formed from the resin composition. The weight ratio of multifunctional benzoxazine(s) to substituted monofunctional benzoxazine may be varied within the range of 99.9:0.1 to 0.1:99.9. In some embodiments, the weight ratio of multifunctional benzoxazine(s) to substituted monofunctional benzoxazine may be 99.9:0.1 to 50:50. Even at high concentration of substituted monofunctional benzoxazine, the composition remains thermally stable (i.e., is not degraded) during curing at temperature equal to or above 180° C., e.g. 180° C.-200° C.

As used herein, a "curable resin composition" refers to a composition prior to curing. Upon curing, the monofunctional and multifunctional benzoxazine compounds readily polymerize via ring opening polymerization. Such polymerization may be initiated cationically (using cationic initiators) or thermally.

The multifunctional benzoxazine may be a compound (monomer or oligomer) in which there are two or more benzoxazine moieties, enabling the formation of cross-linked polymer matrix. Any conventional multifunctional benzoxazine compounds, including di-functional, tri-functional and tetra-functional benzoxazines, may be combined with the substituted monofunctional benzoxazine compounds described above to form a benzoxazine blend.

In one embodiment, the multifunctional benzoxazine may be represented by the following formula (VI):

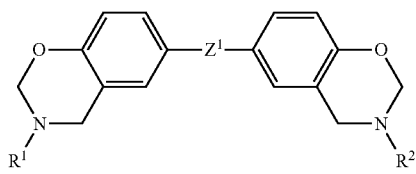

wherein:

$Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings of the benzoxazine moieties may be fused; and $R^1$ and $R^2$ are independently selected from alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on the or each cycloalkyl and aryl group;

$R^3$, $R^4$, $R^5$ and $R^6$ are independently selected from H, $C_{1-8}$ alkyl (preferably $C_{1-4}$ alkyl, and preferably methyl), and halogenated alkyl (wherein the halogen is typically chlorine or fluorine (preferably fluorine) and wherein the halogenated alkyl is preferably $CF_3$); and x and y are independently 0 or 1.

In one embodiment, $Z^1$ is selected from a direct bond, —C($R^3$)($R^4$)—, —C($R^3$)(aryl)-, —C(O)—, —S—, —O—, a divalent heterocycle and —[C($R^3$)($R^4$)]$_x$-arylene-[C($R^5$)($R^6$)]$_y$—, or the two benzyl rings of the benzoxazine moieties may be fused.

Where $Z^1$ is selected from a divalent heterocycle, it is preferably 3,3-isobenzofuran-1(3h)-one, i.e. wherein the compound of formula (VI) is derived from phenolphthalein.

Where $Z^1$ is selected from —[C($R^3$)($R^4$)]$_x$-arylene-[C($R^5$)($R^6$)]$_y$—, then the chain linking the two benzoxazine groups may further comprise, or be optionally interrupted by, one or more arylene group(s) and/or one or more —C($R^7$)($R^8$)— group(s) (where $R^7$ and $R^8$ are independently selected from the groups defined hereinabove for $R^3$), provided that the or each substituted or unsubstituted methylene group is not adjacent to another substituted or unsubstituted methylene group.

In a preferred embodiment, the arylene group is phenylene. In one embodiment, the groups attached to the phenylene group may be configured in para- or meta-positions relative to each other. In a preferred embodiment, the aryl group is phenyl.

The group $Z_1$ may be linear or non-linear, and is typically linear. The group $Z_1$ is preferably bound to the benzyl group of each of the benzoxazine moieties at the para-position relative to the oxygen atom of the benzoxazine moieties, as shown in formula (VI), and this is the preferred isomeric configuration. However, the group $Z_1$ may also be attached at either of the meta-positions or the ortho-position, in one or both of the benzyl group(s) in the bis-benzoxazine compound. Thus, the group $Z_1$ may be attached to the benzyl rings in a para/para; para/meta; para/ortho, meta/meta or ortho/meta configuration. In one embodiment, the thermoset benzoxazine resin component (A) comprises a mixture of isomers, preferably wherein the major portion of the mixture is the para/para isomer shown in formula (VI), and preferably this is present in at least 75 mol %, preferably at least 90 mol %, and preferably at least 99 mol %, of the total isomeric mixture.

In a preferred embodiment, the multifunctional benzoxazine is selected from compounds wherein $Z^1$ is selected from —C($CH_3$)$_2$—, —$CH_2$— and 3,3-isobenzofuran-1 (3H)-one, i.e. benzoxazine derivatives of bisphenol A, bisphenol F and phenolphthalein.

In another embodiment, the multifunctional benzoxazine is selected from compounds wherein $R^1$ and $R^2$ are independently selected from aryl, preferably phenyl. In one embodiment, the aryl group may be substituted, preferably wherein the substituent(s) are selected from $C_{1-8}$ alkyl, and preferably wherein there is a single substituent present on at least one aryl group. $C_{1-8}$ alkyl includes linear and branched alkyl chains. Preferably, $R^1$ and $R^2$ are independently selected from unsubstituted aryl, preferably unsubstituted phenyl.

The benzyl ring in each benzoxazine group of the multifunctional benzoxazine compounds defined herein may be independently substituted at any of the three available positions of each ring, and typically any optional substituent is present at the position ortho to the position of attachment of the $Z^1$ group. Preferably, however, the benzyl ring remains unsubstituted.

Curable Resin Composition and Applications Thereof.

The substituted monofunctional benzoxazine disclosed herein, in isolation or in a blend with one or more multifunctional benzoxazines, may be combined with additional components to form a curable resin composition suitable for the manufacture of resinous films (e.g. adhesive films, surfacing films) or fiber-reinforced composites (e.g. prepregs). The addition of catalysts is optional, but the use of such may increase the cure rate and/or reduce the cure temperatures. Suitable catalysts for the benzoxazine-based resin composition include, but are not limited to, Lewis acids, such as phenols and derivatives thereof, strong acids, such as alkylenic acids, methyl tosylate, cyanate esters, p-toluenesulfonic acid, 2-ethyl-4-methylimidazole (EMI), 2,4-di-tert-butylphenol, $BF_3O(Et)_2$, adipic acid, organic acids, phosphorous pentachloride ($PCl_5$).

Toughening agents (or tougheners) may be added to produce a toughened resin matrix suitable for manufacturing advanced composite structures. Suitable toughening agents include, but are not limited to, thermoplastic toughening agents such as polyethersulphone (PES), co-polymer of PES and polyetherethersulphone (PEES) (e.g. KM 180 from Cytec Industries Inc.), elastomers, including liquid rubbers having reactive groups, particulate toughening agents such as thermoplastic particles, glass beads, rubber particles, and core-shell rubber particles.

Functional additives may also be included to influence one or more of mechanical, rheological, electrical, optical, chemical, flame resistance and/or thermal properties of the cured or uncured resin composition. Examples of such functional additives include, but are not limited to, fillers, color pigments, rheology control agents, tackifiers, conductive additives, flame retardants, ultraviolet (UV) protectors, and the like. These additives may take the form of various geometries including, but are not limited to, particles, flakes, rods, and the like.

In one embodiment, the curable resin composition contains substituted monofunctional benzoxazine in combination with di-functional benzoxazine and tri-functional benzoxazine, and one or more additives discussed above.

The curable resin composition as discussed above may be combined with reinforcement fibers to form a composite material or structure. Reinforcing fibers may take the form of whiskers, short fibers, continuous fibers, filaments, tows, bundles, sheets, plies, and combinations thereof. Continuous fibers may further adopt any of unidirectional, multi-directional, non-woven, woven, knitted, stitched, wound, and braided configurations, as well as swirl mat, felt mat, and chopped-fiber mat structures. The composition of the fibers may be varied to achieve the required properties for the final composite structure. Exemplary fiber materials may include, but are not limited to, glass, carbon, graphite, aramid, quartz, polyethylene, polyester, poly-p-phenylene-benzobisoxazole (PBO), boron, polyamide, graphite, silicon carbide, silicon nitride, and combinations thereof.

It is possible, although not necessary, to add a solvent, for example, a halogenated hydrocarbon or an alcohol, or combination thereof, to aid in the mixing of the components. The solvent and the proportion thereof are chosen so that the mixture of the components forms at least a stable emulsion, preferably a stable single-phase solution. Thereafter, the solvent is removed by evaporation to yield a resin composition.

To form composite materials, the reinforcing fibers are impregnated or infused with the curable resin composition using conventional processing techniques such as prepregging and resin infusion. After resin impregnation or infusion, curing is carried out at elevated temperature up to 200° C., preferably in the range of 160° C. to 200° C., more preferably at about 170° C.-190° C., and with the use of elevated pressure to restrain deforming effects of escaping gases, or to restrain void formation, suitably at pressure of up to 10 bar, preferably in the range of 3 to 7 bar abs. Suitably the cure temperature is attained by heating at up to 5° C./min. for example 2° C. to 3° C./min and is maintained for the required period of up to 9 hours, preferably up to 6 hours, for example 3 to 4 hours. Pressure is released throughout and temperature reduced by cooling at up to 5° C./min. for example up to 3° C./min. Post-curing at temperatures in the range of 190° C. to 200° C. may be performed, at atmospheric pressure, employing suitable heating rates to improve the glass transition temperature of the product or otherwise.

To fabricate prepregs, a resin film may be formed from the curable resin composition by, for example, compression moulding, extrusion, melt-casting or belt-casting, followed by laminating such film to one or both opposing surfaces of a layer of reinforcement fibers in the form of, for example, a non-woven mat of relatively short fibers, a woven fabric of continuous fibers, or a layer of unilaterally aligned fibers (i.e., fibers aligned along the same direction), at temperature and pressure sufficient to cause the resin film to flow and impregnate the fibers. Alternatively, the prepreg may be fabricated by providing the curable resin composition in liquid form, and passing the layer of fibers through the liquid resin composition to infuse the layer of fibers with the heat curable composition, and removing the excess resin from the infused fibrous layer. The presence of substituted monofunctional benzoxazine results in prepregs with improved tack and drape as compared to those formed from the same resin composition without such substituted monofunctional benzoxazine.

To fabricate a composite part from prepregs, plies of impregnated reinforcing fibers are laid up on a tool and laminated together by heat and pressure, for example by autoclave, vacuum or compression moulding, or by heated rollers, at a temperature above the curing temperature of the resin composition or, if curing has already taken place, above the glass transition temperature of the resin, typically, at least 180° C. and up to 200° C., and at a pressure in particular in excess of 1 bar, preferably in the range of 1-10 bar.

The resulting multi-ply layup may be anisotropic in which the fibres are continuous and unidirectional, orientated essentially parallel to one another, or quasi-isotropic in which the fibres in a ply are orientated at an angle, e.g. 45°, 30°, 60° or 90°, relative to those in the plies above and below. Orientations intermediate between anisotropic and quasi-isotropic, and combination thereof, may also be provided. Woven fabrics are an example of quasi-isotropic or intermediate between anisotropic and quasi-isotropic. Suitable layup contains at least 4, preferably at least 8 plies. The number of plies is dependent on the application for the layup, for example, the strength required, and layups containing 32 or even more, for example several hundred, plies may be desirable to form large composite parts. There may be provided toughening interleaf or toughening particles, in the interlaminar regions between plies.

To fabricate a composite part through resin infusion, e.g. RTM or VaRTM processes, the first step is to form a dry fiber preform in the shape of the desired structural part. The preform generally includes a number of fabric layers or plies made from dry reinforcement fibers that impart the desired reinforcing properties to a resulting composite part. After the fiber preform has been formed, the preform is placed in a mold. The curable resin composition is injected/infused directly into fiber preform, and then the resin-infused preform is cured.

EXAMPLES

Example 1

Liquid monofunctional benzoxazines were prepared by the following method:
1. 18.68 g of phenol, 20.94 g of amine and 20.76 g of paraformaldehyde were weighed and then mixed in a glass jar at room temperature (~20.0° C.) for 20 minutes.
2. The blended material was stirred while the glass jar is being placed in an oil bath heated to 115° C. for 40 minutes.
3. The oil bath was increased in temperature to 120° C. and mixing continued for a further 20 minutes.
4. The glass jar was removed from the oil bath and allowed to cool for approximately 5 minutes. The blended material was then slowly added to 10 ml of diethyl ether while stirring. This mixture was then stirred for a further 20 minutes at room temperature (~20.0° C.).
5. Once stirred, the benzoxazine-ether mixture was washed 3 times with 2.0M NaOH solution in water, in 100 ml portions, in a separating funnel.

6. A further water wash was carried out to neutralise the pH (pH7) after the addition of the NaOH.
7. This mixture was left overnight and then magnesium sulphate drying agent added to mixture and dried for 4 hours.
8. Residual ether was removed on a rotary evaporated under vacuum for 15 minutes at 50° C.
9. The final product was dried under vacuum at 60° C. in a vacuum oven for 2 hours.

Table 1 discloses five substituted monofunctional benzoxazines that were prepared by this method using phenol and amine reactants.

3. The jar was immersed in an oil bath heated at 90° C. for 30 minutes and then the blend of materials was stirred at 90° C. for 45 minutes
4. The blend was removed from the oil bath and poured into aluminum dishes.
5. The dishes of blended benzoxazines were degassed in a vacuum oven at 110° C. for 90 minutes.

The degassed benzoxazine blends were cured using the following cure cycle: 25° C. to 180° C. at 1° C./min, held for 2 hours, 180° C. to 200° C. at 1° C./min, held for 2 hours, 200° C. to 25° C. at 2° C./min.

TABLE 1

| Sample | Phenol | Amine | Benzoxazine | Product |
|---|---|---|---|---|
| 1 | 2-fluorophenol | m-toluidine | 8-fluoro-3-(m-tolyl)-3,4-dihydro-2H-benzo[e][1,3]oxazine | Liquid |
| 2 | 3-fluorophenol | m-toluidine | 7-fluoro-3-(m-tolyl)-3,4-dihydro-2H-benzo[e][1,3]oxazine | Liquid |
| 3 | 4-fluorophenol | m-toluidine | 6-fluoro-3-(m-tolyl)-3,4-dihydro-2H-benzo[e][1,3]oxazine | Liquid |
| 4 | 3-chlorophenol | m-toluidine | 7-chloro-3-(m-tolyl)-3,4-dihydro-2H-benzo[e][1,3]oxazine | Liquid |
| 5 | 4-chlorophenol | m-toluidine | 6-chloro-3-(m-tolyl)-3,4-dihydro-2H-benzo[e][1,3]oxazine | Liquid |

Cured samples were prepared by blending liquid monofunctional benzoxazine with Bisphenol-A benzoxazine (a di-functional benzoxazine) from Huntsman Specialty Chemicals at various weight ratios of Bisphenol-A benzoxazine:monofunctional benzoxazine. The following experimental method was carried out:
1. Monofunctional benzoxazine and Bisphenol-A benzoxazine were degassed separately in a vacuum oven at 110° C. for 90 minutes.
2. 1.5 g of the degassed benzoxazine and 18.5 g of the degassed Bisphenol-A benzoxazine were added to a 250 ml glass jar It was found that when the substituted monofunctional benzoxazines (disclosed in Table 1) were blended with Bisphenol-A benzoxazine, the cured samples were stable with increasing concentration of substituted monofunctional benzoxazine. As illustration, FIG. 1 shows cured samples based on blends of Bisphenol A-benzoxazine and 3-fluorophenol, m-toluidine benzoxazine (Structure 2 in Table 1) at different weight ratios of Bisphenol-A benzoxazine:fluorinated benzoxazine.

Figure 2:
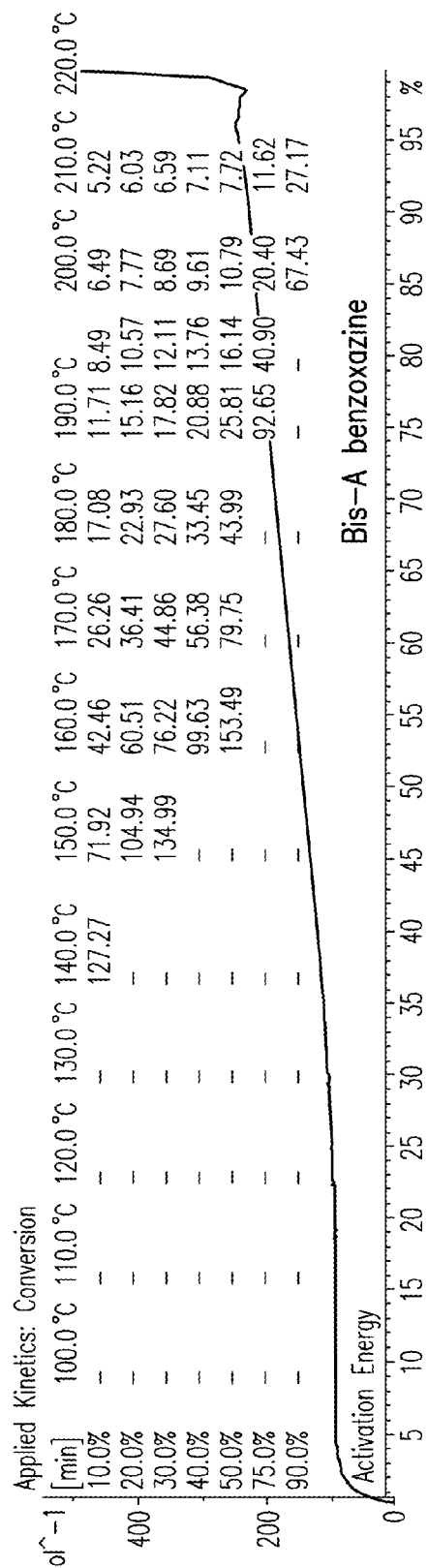
FIG. 2 shows the Differential Scanning calorimetry (DSC) curve and reactivity table for Bisphenol-A benzoxazine.
Figure 3A:
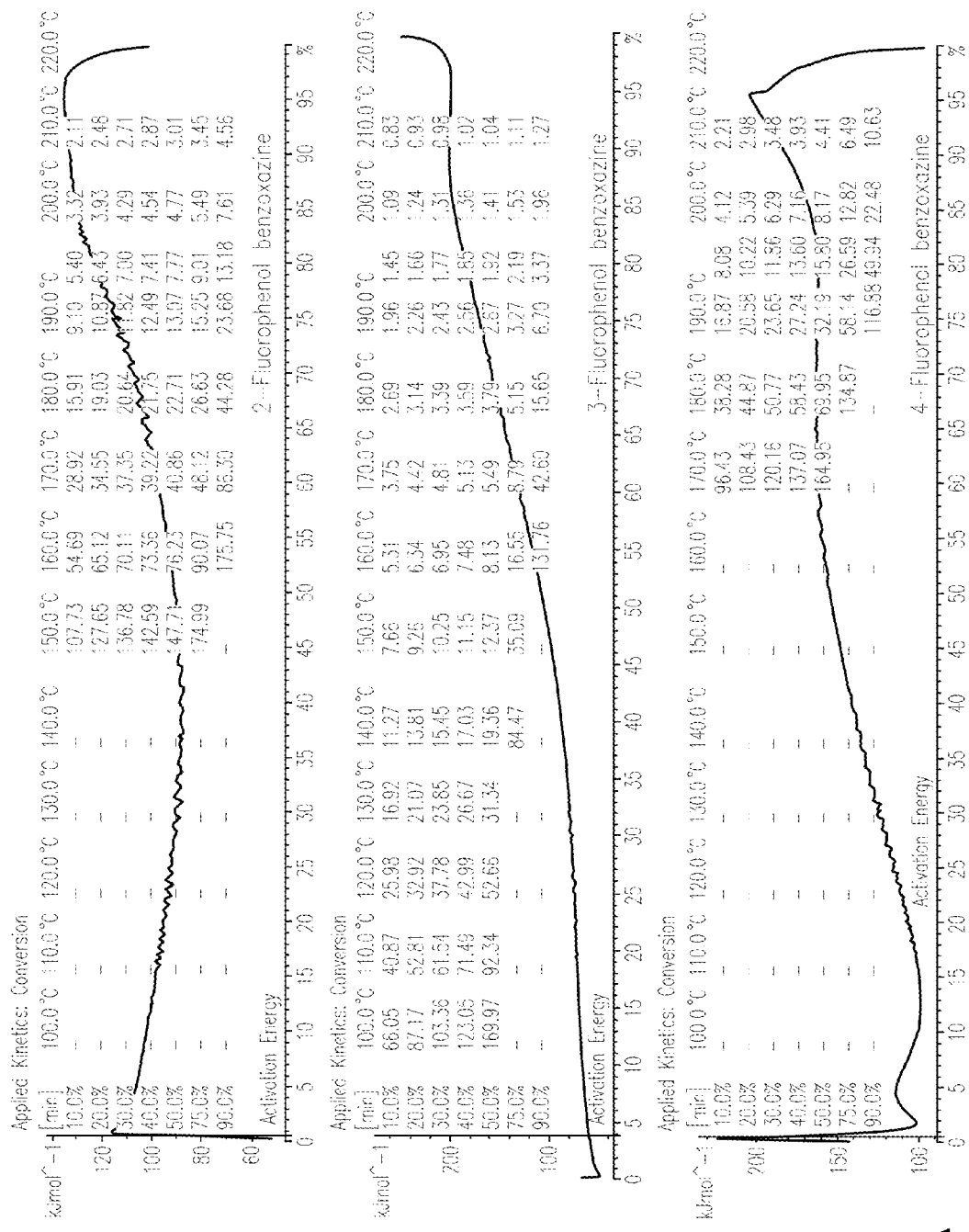
FIG. 3A shows the DSC activation energy curves and reactivity table for certain fluorinated benzoxazines.
Figure 3B:
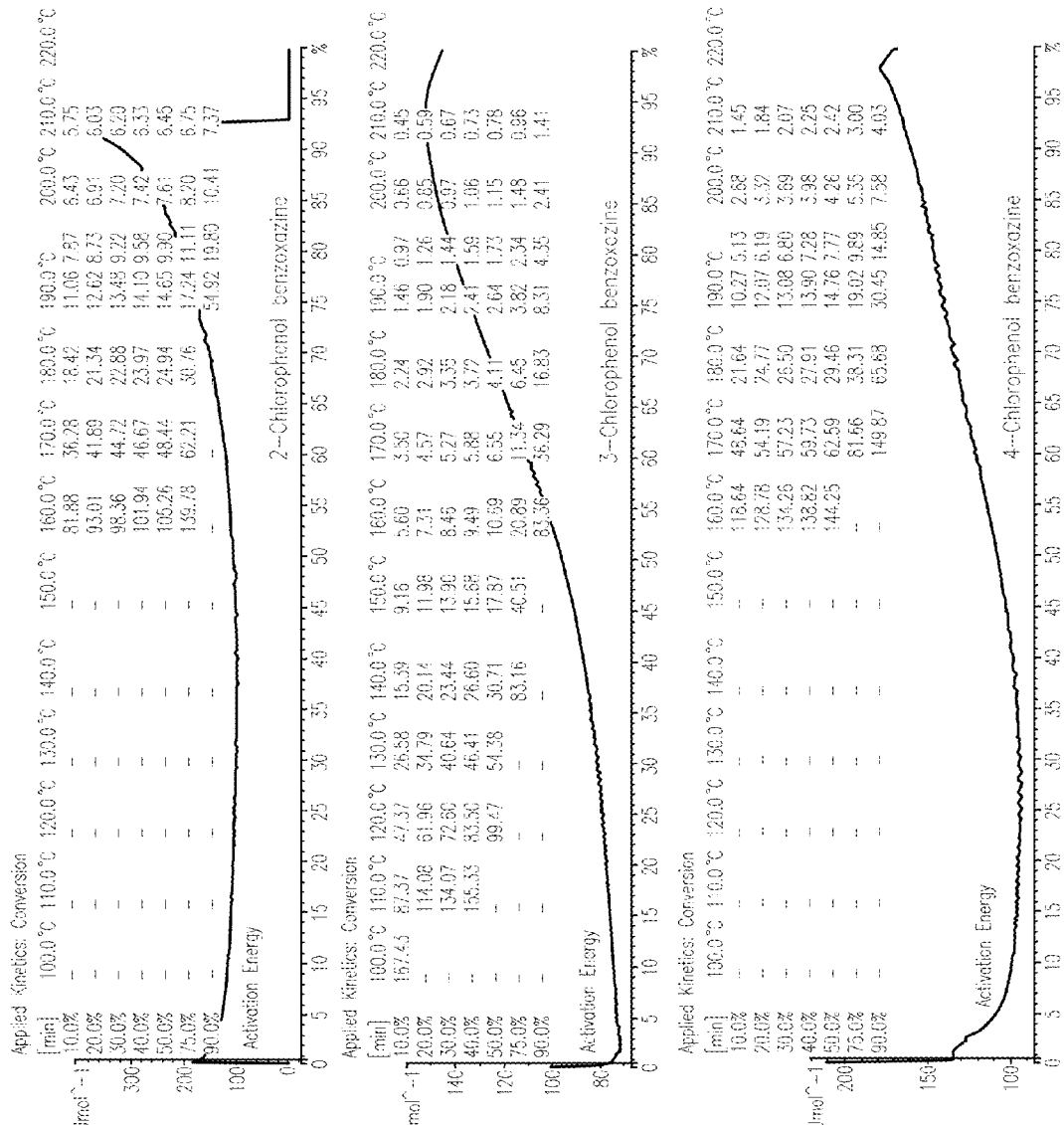
FIG. 3B shows the DSC activation energy curves and reactivity table for certain chlorinated benzoxazines.

An investigation was carried out to analyze the reactivity of the prepared halogenated monofunctional benzoxazine compounds disclosed in Table 1 and compare them to the standard Bisphenol-A benzoxazine using the Model Free Kinetics (MFK)-Differential Scanning calorimetry (DSC) method. This MFK method is based on the assumption that the activation energy, $E_a$, is dependent on the conversion ($\alpha$). At a particular conversion, the activation energy, $E_a$, is independent of the heating rate. FIG. 2 shows the DSC curve for Bisphenol-A benzoxazine. FIG. 3A shows the DSC curves for fluorinated benzoxazines and FIG. 3B shows the DSC curves for chlorinated benzoxazines. It can be seen from FIGS. 2, 3A, and 3B that the effect of the halogen group on reactivity is greatest when it is in the meta position relative to the oxygen.

Example 2

Comparison

For comparison, an alkylated liquid benzoxazine, which does not contain an electron-withdrawing group, was formed from m-cresol, m-toluidine and paraformaldehyde using the method described in Example 1. The alkylated liquid benzoxazine has the following structure:

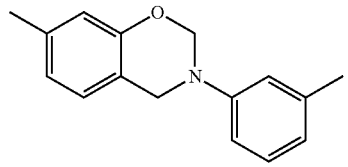

Figure 4:
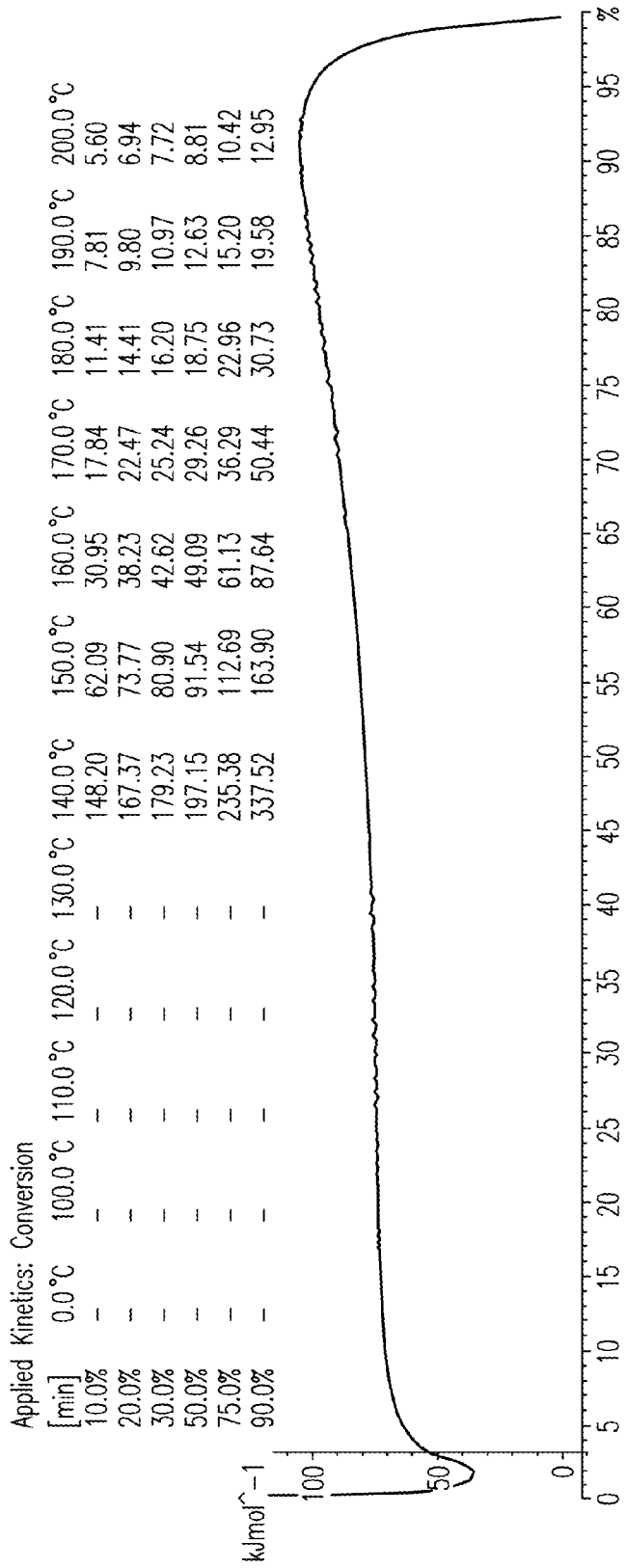
FIG. 4 shows the DSC activation energy curve and reactivity table for an alkylated liquid benzoxazine.

FIG. 4 shows the DSC activation energy curve and reactivity table generated for this alkylated liquid benzoxazine. From FIG. 4, a higher activation energy and a lower conversion rate are seen as compared to the data shown in FIGS. 3A-3B for the halogenated liquid benzoxazines.

Figure 5:
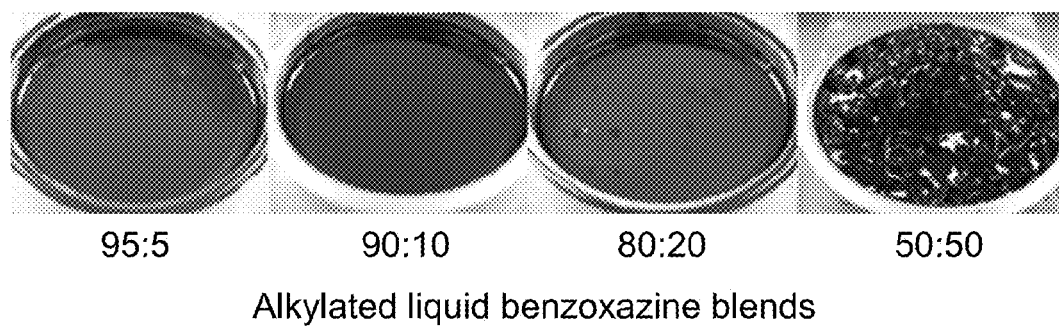
FIG. 5 shows blends of alkylated liquid benzoxazine and Bisphenol-A benzoxazine at different weight ratios.

Blends of alkylated liquid benzoxazine and Bisphenol-A benzoxazine were formed based on Bisphenol-A benzoxazine:alkylated liquid benzoxazine weight ratio of 95:5, 90:10, 80:20, and 50:50. The blends were then cured according the curing cycle described in Example 1. The cured blends are shown in FIG. 5. FIG. 5 shows that the level of stability of the alkylated liquid benzoxazine when cured with Bisphenol-A benzoxazine is decreased with increasing amount of alkylated benzoxazine.

Figure 6:
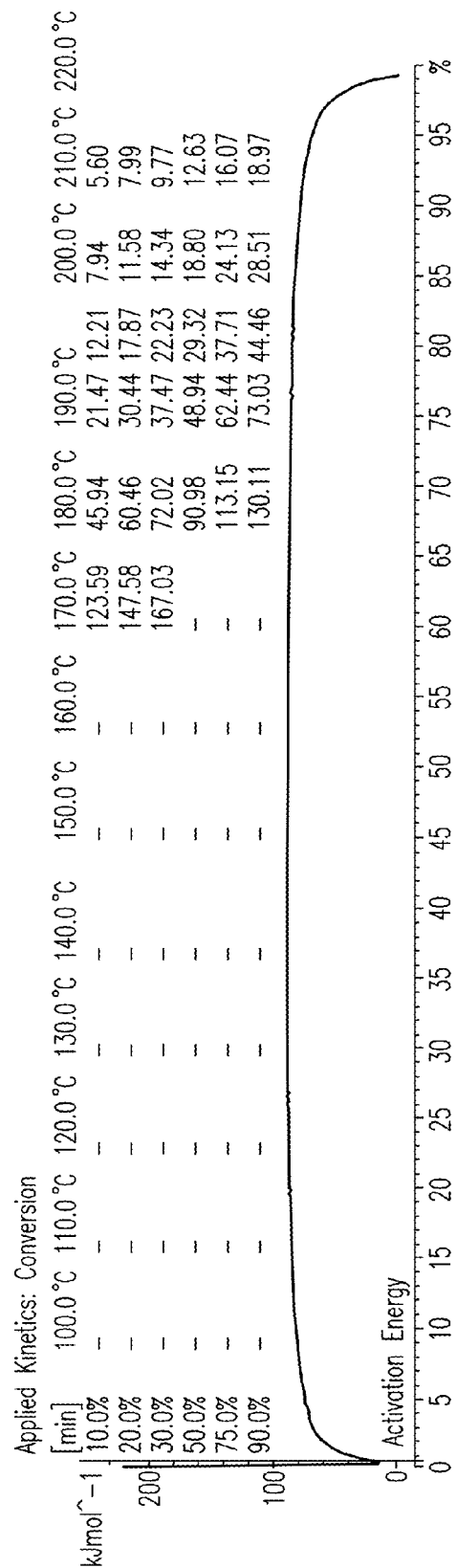
FIG. 6 shows the DSC activation energy curve and reactivity table for a commercially available liquid benzoxazine RD2009-008.

Also for comparison, a commercially available liquid benzoxazine, Huntsman RD2009-008, having the following structure:

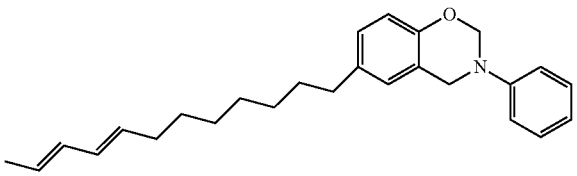 [SMILES: C/C=C/C=C/CCCCCCCc1ccc2c(c1)CN(c1ccccc1)CO2]

was analysed using the MFK-DSC method. FIG. 6 shows the DSC activation energy curve and reactivity table for RD2009-008. From FIG. 6, again a higher activation energy and lower conversion rate are seen as compared to the data shown in FIGS. 3A-3B for the halogenated liquid benzoxazines.

Figure 7:
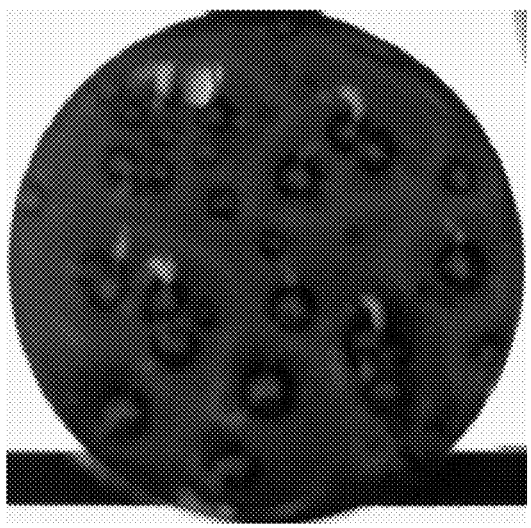
FIG. 7 shows a cured resin sample formed from a blend of RD2009-008 (32%) and Bisphenol-A benzoxazine (68%.)

A blend of 68% Bisphenol-A benzoxazine and 32% RD2009-008 was prepared and cured according to the curing cycle described in Example 1. An image of the cured resin is shown in FIG. 7. FIG. 7 shows that the level of stability of the RD2009-008 material when cured with Bisphenol-A benzoxazine was also decreased.

Figure 8:
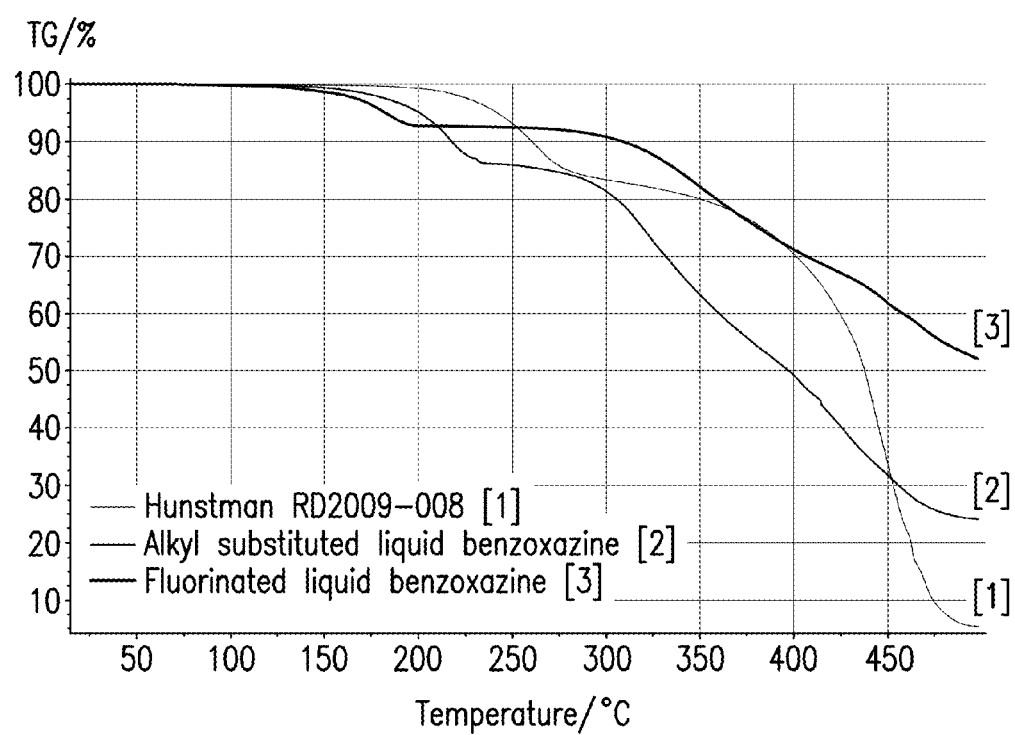
FIG. 8 shows Thermal Gravimetric Analysis (TGA) curves for various liquid benzoxazines.

FIG. 8 shows Thermal Gravimetric Analysis (TGA) curves for RD2009-008, alkylated liquid benzoxazine and fluorinated liquid benzoxazine (Example 1, Structure 2). From FIG. 8, it can be seen that the stability of both the commercial RD2009-008 benzoxazine and the alkylated liquid benzoxazine show greater weight loss in TGA than that for the fluorinated liquid benzoxazine. This corresponds well with the greater stability shown in the optical images of FIG. 1 for fluorinated benzoxazine blends.

When cured, the halogenated liquid benzoxazines also showed higher performance ($T_g$, torsional modulus) than the RD2009-008 benzoxazine blended with Bisphenol-A benzoxazine, see Table 2.

TABLE 2

| Formulation | DMTA tan delta $T_g$ (° C.) | Torsional modulus at 30° C. (GPa) |
|---|---|---|
| Bis-A benzoxazine | 184 | 1.71 |
| Bis-A benzoxazine 68:32 Fluorinated benzoxazine | 189 | 1.72 |
| Bis-A benzoxazine 68:32 Chlorinated benzoxazine | 177 | 1.69 |
| Bis-A benzoxazine 68:32 RD2009-008 liquid benzoxazine | 142 | 1.26 |

Example 3

Tack Test

Samples based on Bis-A Benzoxazine/Epoxy blend, Bis-A benzoxazine/Fluorinated liquid benzoxazine blend, Bis-A benzoxazine/Chlorinated liquid benzoxazine blend were prepared and degassed in a vacuum oven at 110° C. On removal, they were allowed to cool to 80° C., at which time a thumb tack test (thumb placed onto sample) was conducted as the material cooled to 25° C. As a control, pure Bisphenol-A benzoxazine was also subjected to the same degassing conditions and thumb tack test. Table 3 shows the data collected for the tested samples.

TABLE 3

| Components (wt %) | Uncured $T_g$ onset (° C.) | Uncured $T_g$ midpoint (° C.) | Minimum temp. at which tack displayed (° C.) |
|---|---|---|---|
| Bis-A Benzoxazine (100%) | 43.97 | 45.69 | >80 |
| Bis-A Benzoxazine (68%), CY179 epoxy (21%) 4,4'-thiodiphenol (11%) | 46.15 | 58.78 | >80 |
| Bis-A benzoxazine(68%) Fluorinated liquid benzoxazine(32%) | 13.90 | 23.15 | 45 |
| Bis-A benzoxazine (68%) Chlorinated liquid benzoxazine (32%) | 12.86 | 18.29 | 45 |

As can be seen from Table 3, the uncured $T_g$ of the halogenated benzoxazine systems is lower than that of pure Bisphenol-A benzoxazine and that of the Bisphenol-A Benzoxazine/Epoxy blend. This reduction in uncured $T_g$ relates to the malleability of the uncured sample. For an uncured benzoxazine-based material to possess good drape characteristics, the uncured $T_g$ should be approximately at or below room temperature.

Tack testing on the halogenated benzoxazine systems has shown an increase in tack when halogenated liquid benzoxazines were blended with Bisphenol-A benzoxazine as compared to pure Bisphenol-A benzoxazine or to the commercial Bisphenol-A benzoxazine/epoxy blend from Huntsman. The increase in tack and malleability exhibited by the fluorinated and chlorinated benzoxazine blends should allow for easier processability.

Example 4

Figure 9A:
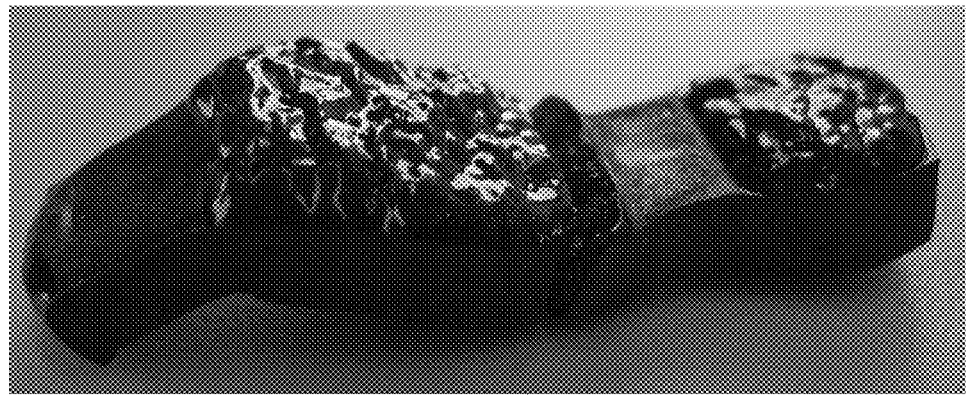
FIGS. 9A-9C show resin samples formed from 100% Bisphenol-A benzoxazine (a), 80:20 Bisphenol-A:3-fluoro benzoxazine (b), and 50:50 Bisphenol-A:3-fluoro benzoxazine (c), after being heated to 300° C.
Figure 9B:
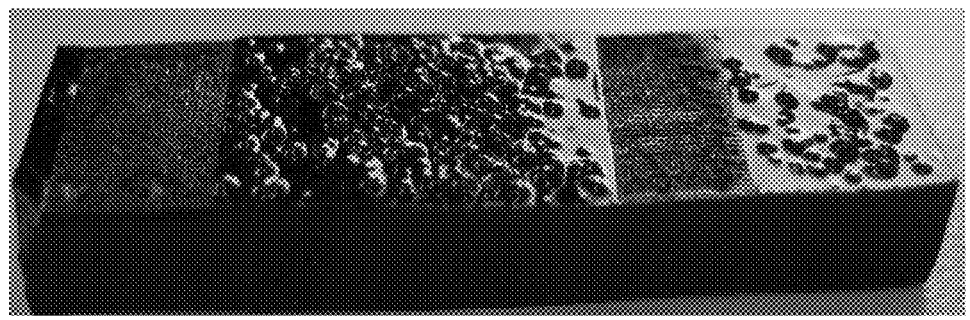
Figure 9C:
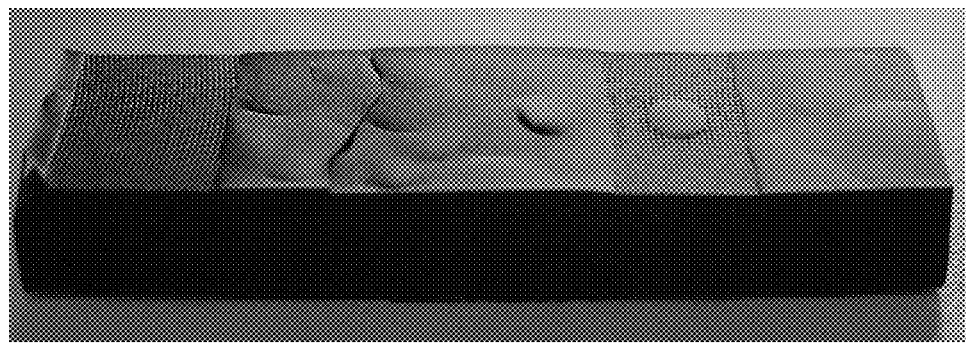

Three samples were prepared based on 100% Bisphenol-A benzoxazine, a blend of Bisphenol-A benzoxazine and 3-fluoro benzoxazine at a weight ratio of 80:20, and the same blend at a weight ratio of 50:50. The samples were then heated to 300° C. FIGS. 9A-9C show that there is an increase in thermal stability at high temperature as the result of adding the fluorinated liquid benzoxazine. In FIGS. 9A-9C, the top image (FIG. 9A) is the image for 100% Bisphenol-A benzoxazine, the middle image (FIG. 9B) is for 80:20 Bisphenol-A:3-fluoro benzoxazine, and the bottom image (FIG. 9C) is for 50:50 Bisphenol-A:3-fluoro benzoxazine.

The benefits described above have been observed with no compromise to the thermo-mechanical performance of the benzoxazine system. Cured samples based on pure Bisphenol-A benzoxazine and blends of Bisphenol-A benzoxazine and 3-fluoro benzoxazine (fluorinated liquid benzoxazine) at different proportions were prepared.

TABLE 4

| Bis-A benzoxazine (%) | 3-Fluoro benzoxazine (%) | DSC midpoint $T_g$ (° C.) | DMTA Tan delta $T_g$ (° C.) | Torsional modulus (GPa) | Flexural modulus (GPa) |
|---|---|---|---|---|---|
| 100 | 0 | 169 | 184 | 1.71 | 5.36 |
| 95 | 5 | 169 | 184 | 1.83 | — |
| 90 | 10 | 170 | 185 | 1.75 | — |
| 80 | 20 | 166 | 186 | 1.75 | — |
| 68 | 32 | 167 | 189 | 1.69 | 5.28 |
| 50 | 50 | 165 | 184 | 1.83 | — |

Table 4 shows that the cured samples of Bisphenol-A/3-fluoro benzoxazine blends retain similar $T_g$ and similar torsional modulus as compared to pure Bisphenol-A benzoxazine. The 68%/32% blend also shows a flexural modulus that is comparable to that of pure Bisphenol A benzoxazine.

In the above Examples, flexural modulus measurements were performed by Intertek MSG in accordance with ASTM method 790-01 (procedure A) and the following conditions:
Instron 5544 (T21)
Load cell 2 kN serial 53033
Test speed 0.01 mm/mm/min
Extensometer Serial B
Micrometer R97
Conditions 23° C.±2° C. r/h 50%±5%
Load cell check weight nos. 1&2 (20N)=40.03N
Glass transition temperature ($T_g$) and torsional modulus of the cured resin samples were measured by Dynamic Mechanical Thermal Analysis (DMTA). Experiments were run on an ARES LS 2K/2K FRT apparatus in torsion rectangular solicitation mode and Dynamic Temperature Ramp Test method, complying with the following experimental conditions: Dynamic Mechanical Thermal Analysis (DMTA) measurements of glass transation temperature ($T_g$) and torsional modulus of the cured resin system were obtained on an ARES LS 2K/2K FRT apparatus in torsional rectangular solicitation mode and dynamic temperature ramp test method, complying with the following experimental conditions:
frequency=0.1 Hz
strain=0.1
heating ramp=3° C./min.
Test samples were in the form of rectangular bars (40× 1.4×4 mm), dried prior to analysis. $T_g$ measurements were recorded at peak tan delta while modulus values were recorded at 30° C. and $T_g$+40° C.

Ranges disclosed herein are inclusive and independently combinable, and is inclusive of the endpoints and all intermediate values within the ranges. For example, the range of "1% to 10%" includes 1%, 2%, 3%, 4%, 5%, 6%, 7%, 8%, 9%, 10% as well as intermediate values such as 1.1%, 1.2%, 1.3%, etc.

While various embodiments are described herein, it will be appreciated from the specification that various combinations of elements, variations of embodiments disclosed herein may be made by those skilled in the art, and are within the scope of the present disclosure. In addition, many modifications may be made to adapt a particular situation or material to the teachings of the embodiments disclosed herein without departing from essential scope thereof. Therefore, it is intended that the claimed invention not be limited to the particular embodiments disclosed herein, but that the claimed invention will include all embodiments falling within the scope of the appended claims.

What is claimed is:
1. A curable composition comprising:
(a) at least one substituted monofunctional benzoxazine compound, which is in liquid form at ambient temperature within the range of 20° C.-25° C. and is represented by one of the following structures:

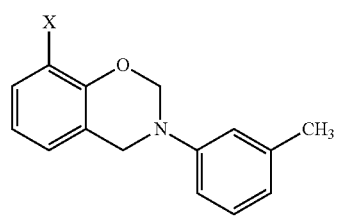

(A)

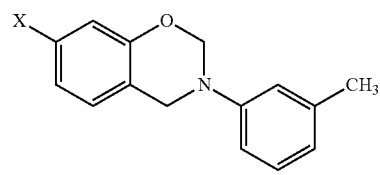

(B)

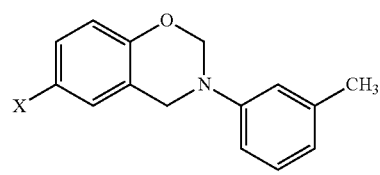

(C)

wherein X is F in structure (A), and is F or Cl in structures (B) and (C); and
(b) at least one multifunctional benzoxazine compound.

2. The curable composition of claim 1, wherein the weight ratio of multifunctional benzoxazine to substituted monofunctional benzoxazine is within the range of 99.9:0.1 to 50:50.

3. The curable composition of claim 2, wherein the multifunctional benzoxazine compound is a di-functional benzoxazine.

4. The of claim 2, wherein the multifunctional benzoxazine compound is a compound of Formula (II):

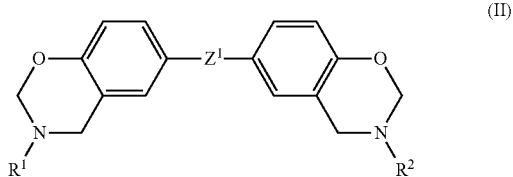

(II)

wherein:
Z$^1$ is selected from a direct bond, —C(R$^3$)(R$^4$)—, —C(R$^3$)(aryl)-, —C(O)—, —S—, —O—, —S(O)—, —S(O)$_2$—, a divalent heterocycle and —[C(R$^3$)(R$^4$)]$_x$-arylene-[C(R$^5$)(R$^6$)]$_y$—, or the two benzyl rings of the benzoxazine moieties may be fused;
R$^1$ and R$^2$ are independently selected from alkyl, cycloalkyl and aryl;
R$^3$, R$^4$, R$^5$ and R$^6$ are independently selected from H, C$_{1-8}$ alkyl and halogenated alkyl;
x and y are independently 0 or 1.

5. The curable composition of claim 4, wherein Z$^1$ is —[C(R$^3$)(R$^4$)]$_x$-arylene-[C(R$^5$)(R$^6$)]$_y$.

6. The curable composition of claim 4, wherein Z$^1$ is selected from —C(CH$_3$)$_2$—, —CH$_2$— and 3,3-isobenzofuran-1(3H)-one.

7. The curable composition of claim 4, wherein R$^1$ and R$^2$ in Formula II are independently selected from aryl.

8. The curable composition of claim 1 further comprising:
at least one thermoplastic or elastomeric toughening agent.

9. The curable composition of claim 1 further comprising:
a catalyst for activating the curing of the benzoxazine compounds.

10. A cured resin formed from curing the curable composition of claim 1 within the range of 180° C.-200° C.

11. A composite material comprising reinforcement fibers impregnated with the curable composition of claim 1.

12. A prepreg comprising a layer of unilaterally aligned reinforcement fibers impregnated with the curable composition of claim 1.

13. A composite part formed by infusing a dry fiber preform having a three-dimensional shape with the curable composition of claim 1, followed by curing.

14. The curable composition of claim 1, wherein the substituted monofunctional benzoxazine compound is represented by structure (B) and the composition further comprises an isomer represented by structure (D):

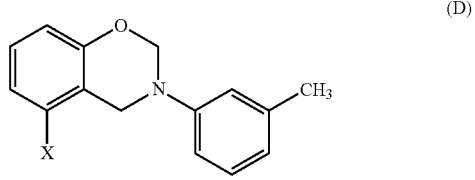

(D)

wherein X is the same for both structures (B) and (D).

15. The curable composition of claim 1, wherein the composition does not contain any solvent.

* * * * *